United States Patent [19]

Kaminuma et al.

[11] Patent Number: 5,612,454

[45] Date of Patent: Mar. 18, 1997

[54] PROCESS FOR PURIFICATION OF POLYPEPTIDE USING A BUCHNER FUNNEL

[75] Inventors: Toshihiko Kaminuma; Toshii Iida; Masahiro Tajima, all of Yokohama, Japan

[73] Assignee: Shiseido Company Ltd., Tokyo, Japan

[21] Appl. No.: 776,272

[22] PCT Filed: Mar. 29, 1991

[86] PCT No.: PCT/JP91/00421

§ 371 Date: Nov. 29, 1991

§ 102(e) Date: Nov. 29, 1991

[87] PCT Pub. No.: WO91/15502

PCT Pub. Date: Oct. 17, 1991

[30] Foreign Application Priority Data

Mar. 30, 1990 [JP] Japan ........................... 2-86898
Aug. 10, 1990 [JP] Japan ........................... 2-213016

[51] Int. Cl.$^6$ ........................... A61K 38/00; A61K 38/02; C07K 1/00; C07K 5/00
[52] U.S. Cl. ........................... 530/344; 530/324; 530/325; 530/326; 530/300
[58] Field of Search ........................... 530/324, 325, 530/326, 344, 300; 514/12

[56] References Cited

U.S. PATENT DOCUMENTS 4,894,330  1/1990  Hershenson et al. ............... 435/69.51

FOREIGN PATENT DOCUMENTS 0146842  12/1984  European Pat. Off. .
1502556   9/1989  Japan .

OTHER PUBLICATIONS

Raikher et al., Chemical Abstracts, vol. 102 No. 5, p. 411, Ab No: 43971j, Feb. 1985.

Analytical Biochemistry, (vol. 148) No. 1, Jul. 1985 pp. 93–100; Hans Peter Nick et al.

Birnbaum et al, J. Biol Chem., vol. 258, No. 9, May 10, 1983, pp. 5463–5466.

Wasserman et al., J. of Chromatography, vol. 411, pp. 345–354, 1987.

R. S. Birnbaum eta l., "Purification and Amino Acid Sequence of a Noncalcitonin Secretory Peptide Derived from Preprocalcitonin", J. Biol. Chem., vol. 258, No. 9, pp. 5463–5466, (1983).

G. Folena–Wasserman et al., "Assay, Purification and Characterization of a Recombinant Malaria Circumsporozoite Fusion Protein by High–Performance Liquid Chromtatography", J. Chromatogr., vol. 411 . . . .

M. Ohmori et al., "Genetic Construction and High–Level Gene Expression in *Escherichia coli* of a Precursor of Salmon Calcitonin I", Agric. Biol. Chem., vol. 52, No. 11, pp. 2823–2830, (1988).

J. S. Soldin et al., "Rapid Micromethod for Measuring Anticonvulsant Drugs in Serum by High–Performance Liquid Chromatography", Clin. Chem., vol. 22, No. 6, pp. 856–859, (1976).

*Primary Examiner*—Avis M. Davenport
*Attorney, Agent, or Firm*—Foley & Lardner

[57] ABSTRACT

An improved process for purifying a polypeptide using a packing material for reversed phase high performance liquid chromatography is provided. A process for purifying a polypeptide characterized in that an aqueous solution containing polypeptide obtained by pre-treating a polypeptide produced by a wide variety of cells to a predetermined state is adjusted to a specific pH value, to remove impurities, and is then treated with a packing material for reversed phase high performance liquid chromatography.

1 Claim, 8 Drawing Sheets

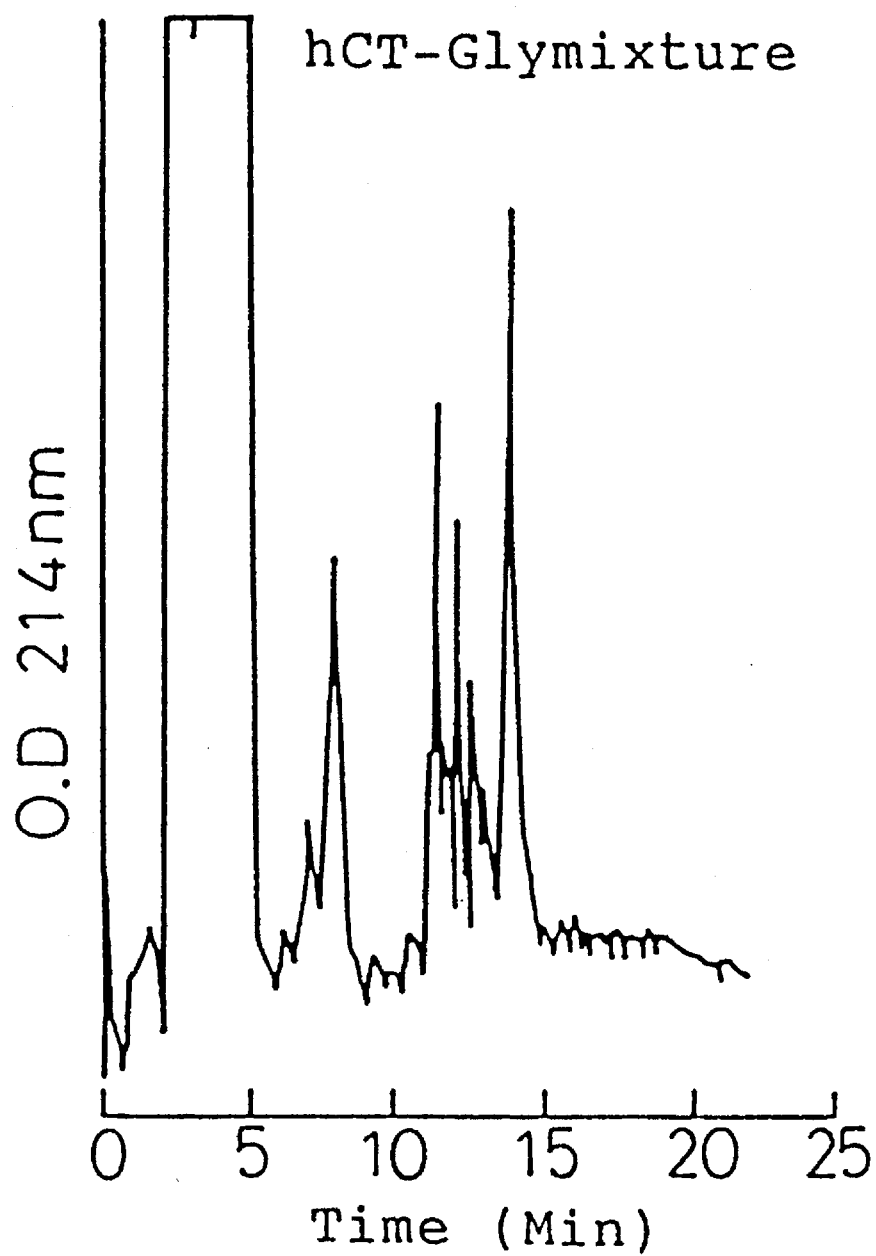

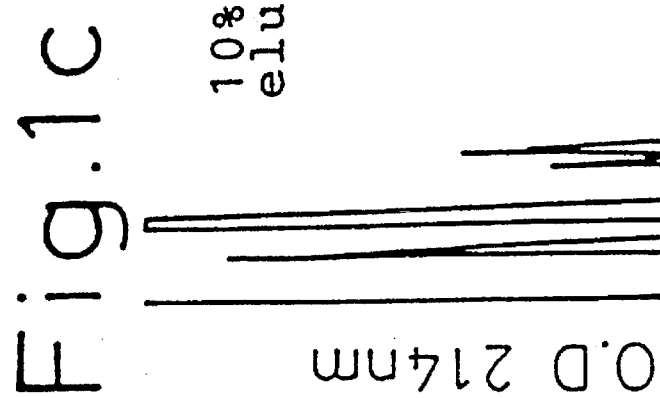
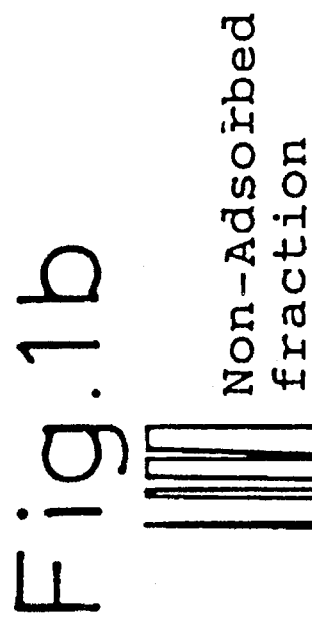

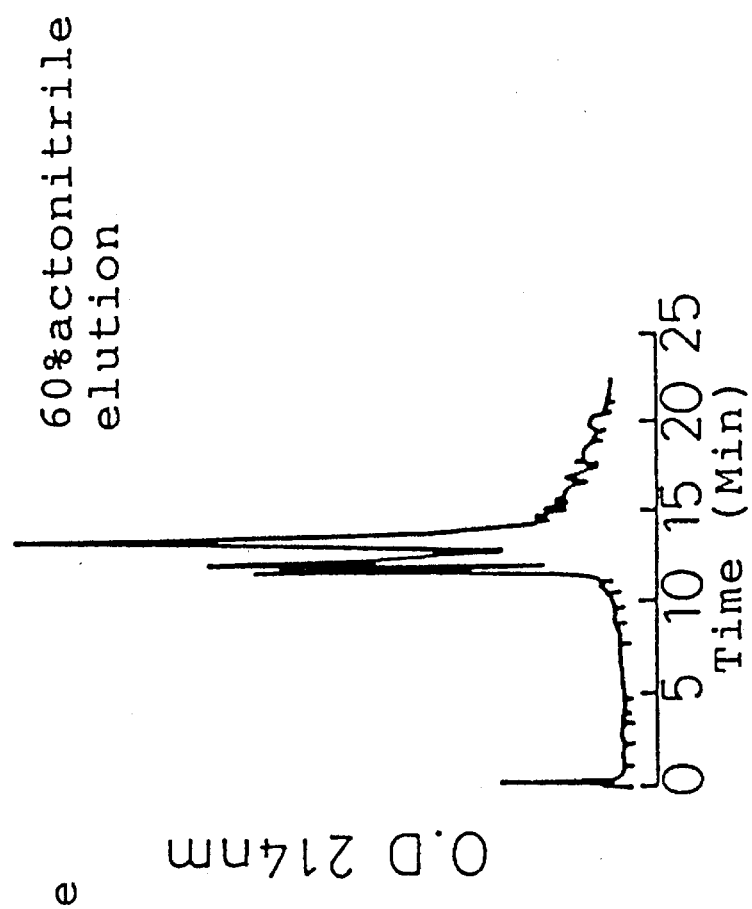
Fig.1d
Fig.1e
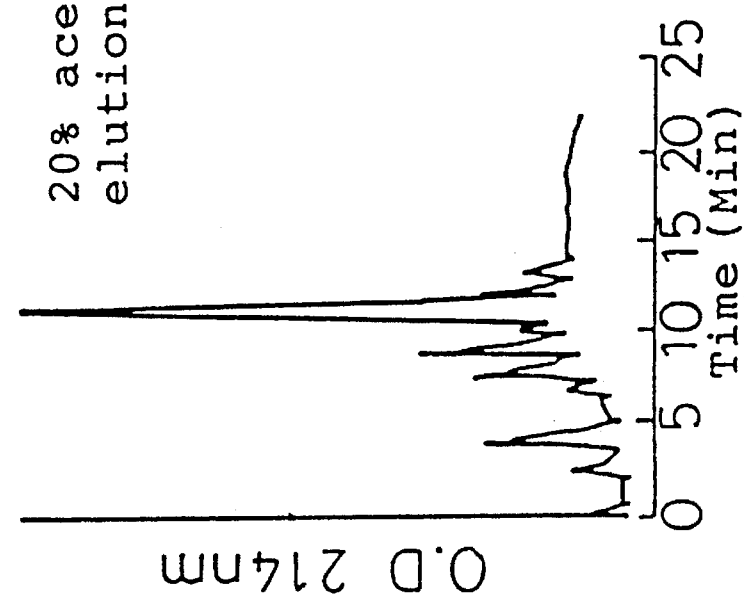

PROCESS FOR PURIFICATION OF POLYPEPTIDE USING A BUCHNER FUNNEL

[TECHNICAL FIELD]

The present invention relates to an improved process for purifying a polypeptide, more specifically, to a purification process carried out by subjecting an objective substance containing a polypeptide to a pretreatment, and then treating the resulting crude polypeptide aqueous solution with a packing material for reversed phase high performance liquid chromatography.

[BACKGROUND ART]

A very complicated proceudure is required to purify polypeptides produced by microorganisms, animal cells, and plant cells, while maintaining their physiological activities to high degree. Consequently, the present procedures require some to be improvement. For example, the purification of a human growth hormone releasing factor produced by transformed microorganisms involves a ten stage procedure, resulting in a large amount of production but at a yield too low for carrying out a bioassay (Vincent Geli et al., Gene, 80, 129–136 (1989)). For the purification of human calcitonin, it has been reported that an eight stage purification is carried out, using 6 types of columns, to isolate human calcitonin (J. P. Gilligan et al., Biochromatography, 2 (1), 20–27 (1987)).

These purification steps, however, are very complicated, and thus it may be considered that they lead to the decomposition of polypeptides, and to the disappearance of physiological activities of polypeptides during the purification.

The object of the present invention is, therefore, to provide a process which can isolate polypeptides in a stable form and isolate and purify polypeptides at a high yield by carrying out a simple procedure, in order to thus solve these problems.

[DISCLOSURE OF THE INVENTION]

Over the past several years, various physiologically active polypeptides, represented by the human growth hormone and human calcitonin, have been increasing produced with the aid of various cells manufactured by a genetic procedure. Of these, in addition to naturally found types of physiologically active polypeptides per se, there are many polypeptides produced as fused polypeptides (also referred to as "chimera proteins") to which other protein moieties are fused. Although these can be purified by using a conventional separation/purification process, there has been a particularly desire for the development of a process for efficiently recovering objective physiologically active polypeptides without any deactivation after cleaving fused polypeptides into physiologically active moieties and other protein moieties fused thereto. The present inventors found that, when the cleaved substances of the above-mentioned fused polypeptides are treated under a specific pH level, and the treated liquid thus obtained is treated with a packing material for reversed phase high performance liquid chromatography, objective physiologically active polypeptides can be efficiently obtained, and that this process also can be advantageously used for purifying samples containing physiologically active polypeptides per se, to thereby accomplished the present invention.

The above-mentioned object can be achieved by providing a process for purifying a polypeptide of the present invention, which process involves the following stages. That is, the present invention concerns a process which comprises (a) a stage for regulating the pH range of an aqueous solution containing a crude polypeptide to 1–4 to cause impurities to precipitate, followed by removing these impurities, and (b) adsorbing the supernatant obtained in the above-mentioned stage (a) on a packing material for reversed phase high performance liquid chromatography, followed by eluting an objective polypeptide.

[BRIEF DESCRIPTION OF THE DRAWINGS]

FIGS. 1 (a)–(e) show HPLC elution patterns of human calcitonin precursor solutions purified according to the process of the present invention accoding to stage order;

[BEST MODE OF CARRYING OUT THE INVENTION]

Figure 2:
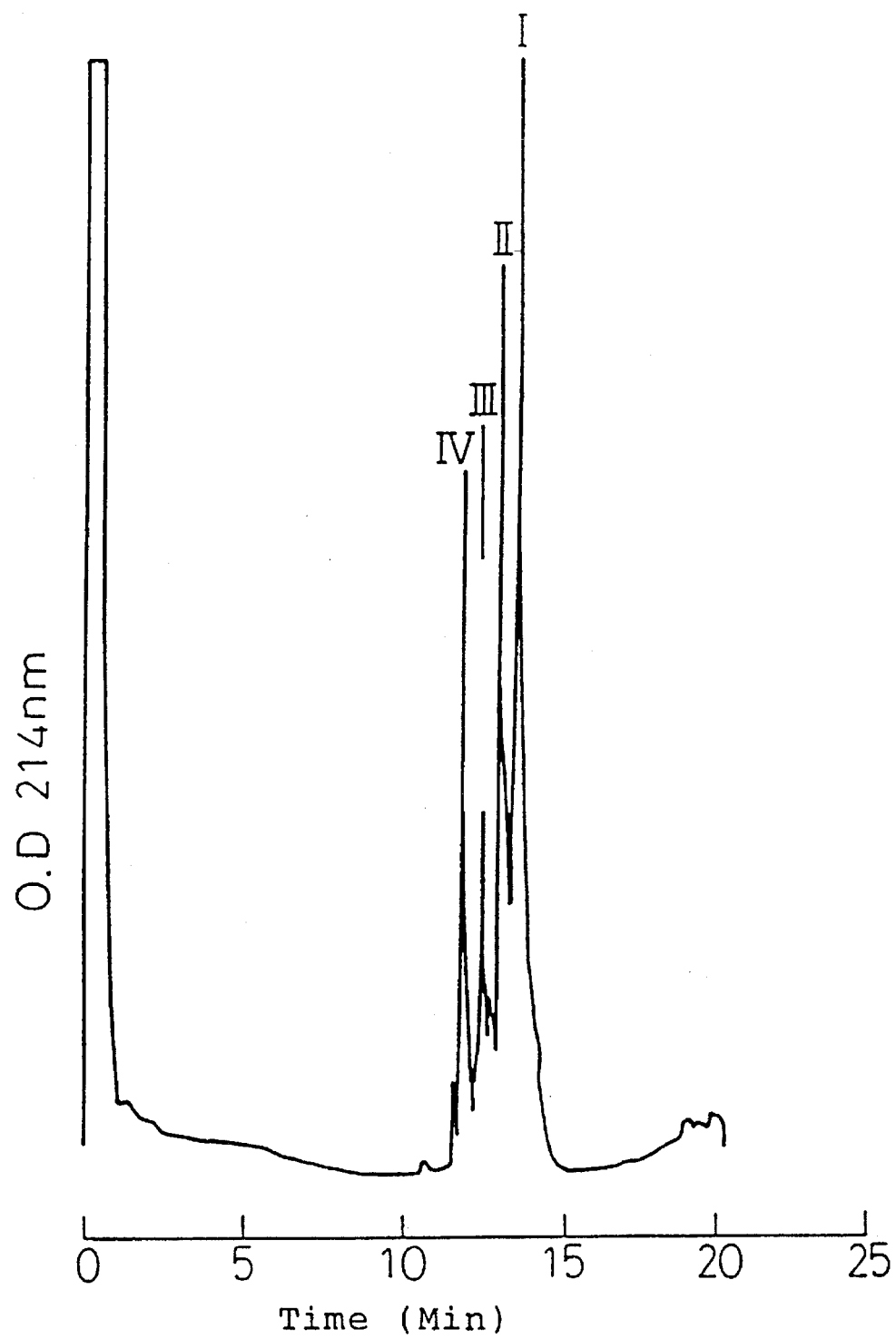
FIG. 2 shows an HPLC elution pattern of the specimen of FIG. 1 (e) after having been freeze-dried.

The polypeptides to be purified according to the present invention may originate from microorganisms, animal cells and plant cells, or from these cells which have been subjected to a genetic procedure for producing prescribed polypeptides. Consequently, the purification process of the present invention is aimed at treated substances (e.g. homogenates) and/or cultures of the above-mentioned cells.

Before these treated substances and/or cultures are subjected to the process of the present invention, cell homogenated substances or the cells themselves are removed, objective physiologically active polypeptides are solubilized in an aqueous medium, and optionally are concentrated, to be purified in a separation/purification process known per se. Where the physiologically active polypeptides are obtained from the above-mentioned origins in the fused polypeptide form, they are purified according to the process of the present invention, after being purified to a considerably high degree in the fused polypeptide form, and then are cleaved into the physiologically active moieties and other protein moieties. Therefore, the term "aqueous solution containing crude polypeptides" used in the present invention includes a wide variety of treated liquid coming from the above-mentioned origins, and they can applied in any purification stage as long as the effect of the present invention is exhibited. One kind of solution which can be advantageously treated according to the process of the present invention includes, but is not limited to, a reaction solution after fused polypeptides are cleaved into the physiologically active moieties and other protein moieties.

The treated substances and/or cultures of the above-mentioned cells can be prepared by a process for producing polypeptides known per se.

For example, the outline for the production of polypeptide using an expression vector is as follows:

As hosts which express genes coding for polypeptides, microorganisms such as *E. coli, Bacillus subtilis,* yeasts; animal cells such as those originating from insects, mammals, and the amphiba; and plant cells can be mentioned. As the expression vector, any plasmid can be used as long as it can effectively express a gene including an objective polypeptide in the cells. For examples, it can be suitably selected from among plasmids described in the following literature: Vector DNA, the 1st press (1986), edited by Yoshiyuki Sakaki., Kodansha; Zoku Seikagaku Jikken Koza I, Idenshi Kenkyuhou II (How to Research Gene II),— Kumikae DNA Gijutsu (DNA Recombination Technique)—, Chapter 7, Kumikaetai no Hatsugen (Expression of Recombinants), edited by Society of Biochemical Society of Japan, Tokyo Kagaku Dojin; Recombinant DNA, Part D, Section II, Vectors for Expression of Cloned Gene, (1987), edited by Ray Wu and Lawrence Grossman, Academic Press, INC: Molecular Cloning, A Laboratory Manual 2nd Ed, Book 3, (1989), edited by J. Sambrook, E. P. P. Pritsch and T. Maniatis, Cold Spring Harbor Laboratory Press; etc.

For example, in the case of *E.coli,* pMb, pBR, and pUC type vectors, for yeasts, YIp, YRp, or YEp type vectors, and for *Bacillus subtilis,* pUB, pBC, or pBD types can be used. For animal cells, SV 40, BKV, or BPV types can be used. For plant cells, the same vectors as those in the case of *E. coli*, with the exception that the prompters are changed to those which work on the plants, can be used. Examples of the promoters working on the plants include promoters for chlorophyll a-b binding proteins, cauliflower mosaic virus 35S, and the like.

The recombination of these vectors, and the transformation and transduction of the host cell with the recombinant plasmids can be carried out by procedures known per se described in the above-mentioned literature, etc., respectively. The transformed cells thus obtained can be cultivated in a medium under the culture condition usually used for growing the cell to be treated.

Where the polypeptides and/or fused polypeptides from such cultivated substances are secreted extracellularly, the cells are removed, and where they are accumulated in the cell, after the culture is removed, the polypeptides and/or fused polypeptides are collected by cell homogenization, etc.

Although not intended to be restricted, the polypeptides at which the purification according to the present invention is aimed are those in which two or more amino acids are peptide-bonded. Also the term "polypeptides" intended herein include modified polypeptides, such as the polypeptides in which saccharide or phosphoric acid is bonded to their amino acids and polypeptides whose N-terminal side is amidated, etc. Such polypeptides possess a molecular weight of not more than 15,000, and include, for example, hormones and growth factors such as insulin, growth hormone release factor (GRF), epidermal growth factor (EGF), atrial natriuretic peptide (ANP), thymosin $\alpha_1$, thymosin $\beta_4$, thymopoietin, transforming growth factor (TGF-$\alpha$), adrenocorticotropic hormone (ACTH), calcitonin gene-related peptide (CGRP), and cartilage factor (CDF); and cytokinins such as interleukin-2 and interleukin-3. Polypeptides which can be preferably applied to the process of the present invention other than these polypeptides include the polypeptides listed below.

As an explanation of the polypeptides, when amino acids and other things are displayed as abbreviations, they are displayed according to IUPAC rules or by symbols usual in this field. Some examples thereof are listed below.

Ser: L-serine

Leu: L-leucine

Arg: L-arginine

Cys: L-cysteine

Gln: L-glutamine

Lys: L-Lysine

Ile: L-isoleucine

Pro: L-proline

Val: L-valine

His: L-histidine

Met: L-methionine

Ala: L-alanine

Gly: Glycine

Phe: L-phenylalanine

Asp: L-aspartic acid

Asn: L-asparagine

Glu: L-glutamic acid

Trp: L-tryptophan

Thr: L-threonine

Tyr: L-tyrosine x: any one of the above-mentioned amino acids hCT: human calcitonin CT: calcitonin HPLC: high performance liquid chromatography (1) Angiotensin II which can be used as an angiotonic or a hypertensioning agent (origining from equine)

Asp-Arg-Val-Tyr-Ile-His-Pro-Phe (L. T. Skeggs et al., J. Exptl. Med, 106, 439, 1957)

(2) Angiotensin II antagonist known as a hypotensor

Ser-Arg-Val-Tyr-Val-His-Pro-Ala (3) Angiotensin III

Arg-Val-Tyr-Ile-His-Pro-Phe (Campbell. W. B. et al., Science, 184, 994, 1974)

(4) C-Terminal glycine adduct of calcitocin known as know as a hyperkalemia treating agent (precursor for C-terminal amidation)

(Human)

Cys-Gly-Asn-Leu-Ser-Thr-Cys-Met-Leu-
Gly-Thr-Tyr-Thr-Gln-Asp-Phe-Asn-Lys-
Phe-His-Thr-Phe-Pro-Gln-Thr-Ala-Ile-
Gly-Val-Gly-Ala-Pro-Gly (Swine)

Cys-Ser-Asn-Leu-Ser-Thr-Cys-Val-Leu-
Ser-Ala-Tyr-Trp-Arg-Asn-Leu-Asn-Asn-
Phe-His-Arg-Phe-Ser-Gly-Met-Gly-Phe-
Gly-Pro-Glu-Thr-Pro-Gly (Bovine)

Cys-Ser-Asn-Leu-Ser-Thr-Cys-Val-Leu-
Ser-Ala-Tyr-Trp-Lys-Asp-Leu-Asn-Asn-
Tyr-His-Arg-Phe-Ser-Gly-Met-Gly-Phe-
Gly-Pro-Glu-Thr-Pro-Gly (Salmon)

Cys-Ser-Asn-Leu-Ser-Thr-Cys-Val-Leu-
Gly-Lys-Leu-Ser-Gln-Glu-Leu-His-Lys-

Leu-Gln-Thr-Tyr-Pro-Arg-Thr-Asn-Thr-
Gly-Ser-Gly-Thr-Pro-Gly
(Rabit)
Cys-Ser-Asn-Leu-Ser-Thr-Cys-Val-Leu-
Gly-Lys-Leu-Ser-Gln-Glu-Leu-His-Lys-
Leu-Gln-Thr-Tyr-Pro-Arg-Thr-Asp-Val-
Gly-Ala-Gly-Thr-Pro-Gly
(Avian)
Cys-Ala-Ser-Leu-Ser-Thr-Cys-Val-Leu-
Gly-Lys-Leu-Ser-Gln-Glu-Leu-His-Lys-
Leu-Gln-Thr-Tyr-Pro-Arg-Thr-Asp-Val-
Gly-Ala-Gly-Thr-Pro-Gly
(Lasmoles. F., et al., FEBS lett. 180, 113, 1985)

(5) Melanocyte-stimulating hormone having a melanocyte-stimulating effect, α-MSH
Ser-Tyr-Ser-Met-Glu-His-Phe-Arg-Trp-
Gly-Lys-Pro-Val
(Harris, J. I. et al., Nature, 179, 1346, 1957)

(6) Melanocyte-stimulating hormone, β-MSH (Squalidae)
Asp-Gly-Asp-Asp-Tyr-Lys-Phe-Gly-His-
Phe-Arg-Trp-Ser-Val-Pro-Leu
(Bennet, H. P. J. et al., Biochem. J., 141, 439, 1974)

(7) Trypsin inhibitor
(Human)
Asp-Ser-Leu-Gly-Arg-Glu-Ala-Lys-Cys-
Tyr-Asn-Glu-Leu-Asn-Gly-Cys-Thr-Lys-
Ile-Tyr-Asn-Pro-Val-Cys-Gly-Thr-Asp-
Gly-Asp-Thr-Tyr-Pro-Asn-Gly-Cys-Val-
Leu-Cys-Phe-Glu-Asn-Arg-Lys-Arg-Gln-
Thr-Ser-Ile-Leu-Ile-Gln-Lys-Ser-Gly-
Pro-Cys
(Bartelt. D. C. et al., Arch. Biochem. Biophys., 179, 189, 1977)
(Bovine)
Asn-Ile-Leu-Gly-Arg-Glu-Ala-Lys-Cys-
Thr-Asn-Glu-Val-Asn-Gly-Cys-Pro-Arg-
Ile-Tyr-Asn-Pro-Val-Cys-Gly-Thr-Asp-
Gly-Val-Thr-Tyr-Ser-Asn-Glu-Cys-Leu-
Leu-Cys-Met-Glu-Asn-Lys-Glu-Arg-Gln-
Thr-Pro-Val-Leu-Ile-Gln-Lys-Ser-Gly-
Pro-Cys
(Greene, L. J. et al., J. Biol. Chem. 244, 2646, 1969)

(8) Accessory thyroid hormone having calcium release effect
(Swine)
Ser-Val-Ser-Glu-Ile-Gln-Leu-Met-His-
Asn-Leu-Gly-Lys-His-Leu-Ser-Ser-Leu-
Glu-Arg-Val-Gln-Trp-Leu-Arg-Lys-Lys-
Leu-Gln-Asp-Val-His-Asn-Phe-Val-Ala-
Leu-Gly-Ala-Ser-Ile-Val-His-Arg-Asp-
Gly-Gly-Ser-Gln-Arg-Pro-Arg-Lys-Lys-
Glu-Asp-Asn-Val-Leu-Val-Glu-Ser-His-
Gln-Lys-Ser-Leu-Gly-Glu-Ala-Asp-Lys-
Ala-Ala-Val-Asp-Val-Leu-Ile-Lys-Ala-
Lys-Pro-Gln
(Brewer, H. B., et al., Amer. J. Med., 56, 759, 1974)

(9) Avoidance inducing hypophysis peptide
(Swine)
Cys-Tyr-Phe-Gln-Asn-Cys-Pro-Lys
(Lande, S., et al., J. Biol. Chem., 246, 2058, 1971)

(10) Proinsulin C peptide
(Bovine)
Glu-Val-Glu-Gly-Pro-Gln-Val-Gly-Ala-
Leu-Glu-Leu-Ala-Gly-Gly-Pro-Gly-Ala-
Gly-Gly-Leu-Glu-Gly-Pro-Pro-Gln
(Salokangas, A. et al., Eur. J. Biochem., 20, 813, 1971)

(11) Insulin-like growth factor I known as a cell growth promoting factor
Gly-Pro-Glu-Thr-Leu-Cys-Gly-Ala-Glu-
Leu-Val-Asp-Ala-Leu-Gln-Phe-Val-Cys-
Gly-Asp-Arg-Gly-Phe-Tyr-Phe-Asn-Lys-
Pro-Thr-Gly-Tyr-Gly-Ser-Ser-Ser-Arg-
Arg-Ala-Pro-Gln-Thr-Gly-Ile-Val-Asp-
Glu-Cys-Cys-Phe-Arg-Ser-Cys-Asp-Leu-
Arg-Arg-Leu-Glu-Met-Tyr-Cys-Ala-Pro-
Leu-Lys-Pro-Ala-Lys-Ser-Ala
(Rinderknecht, E. et al., Proc. Natl. Acad. Sci. USA, 73, 4379, 1976)

(12) Pancreatic polypeptide
(Avian)
Gly-Pro-Ser-Gln-Pro-Thr-Tyr-Pro-Gly-
Asp-Asp-Ala-Pro-Val-Glu-Asp-Leu-Ile-
Arg-Phe-Tyr-Asp-Asn-Leu-Gln-Gln-Tyr-
Leu-Asn-Val-Val-Thr-Arg-His-Arg-Tyr
(Kimmel, J. R. et al., J. Biol. Chem., 250, 9369, 1978)

(13) Peptides bound a glycyl group to calcitonin gene-related peptides at the C-terminal amino acid residue (precursors for C-terminal amidation)

(Human α type)
Ala—Cys—Asp—Thr—Ala—Thr—Cys—Val—Thr—His—Arg—Leu—
Ala—Gly—Leu—Leu—Ser—Arg—Ser—Gly—Gly—Val—Val—Lys—
Asn—Asn—Phe—Val—Pro—Thr—Asn—Val—Gly—Ser—Lys—Ala—
Phe—Gly
(Morris et al., Nature, 308,746 (1984))

(Human β type)
Ala—Cys—Asn—Thr—Ala—Thr—Cys—Val—Thr—His—Arg—Leu—
Ala—Gly—Leu—Leu—Ser—Arg—Ser—Gly—Gly—Met—Val—Lys—
Ser—Asn—Phe—Val—Pro—Thr—Asn—Val—Gly—Ser—Lys—Ala—
Phe—Gly
(Steenberg et al., FEBS Lett, 183,403 (1985))

(Rat α type)

Ser—Cys—Asn—Thr—Ala—Thr—Cys—Val—Thr—His—Arg—Leu—
Ala—Gly—Leu—Leu—Ser—Arg—Ser—Gly—Gly—Val—Val—Lys—
Asp—Asn—Phe—Val—Pro—Thr—Asn—Val—Gly—Ser—Glu—Ala—
Phe—Gly (Amara et al., Nature, 298,240 (1982))

(Rat β type)

Ser—Cys—Asn—Thr—Ala—Thr—Cys—Val—Thr—His—Arg—Leu—
Ala—Gly—Leu—Leu—Ser—Arg—Ser—Gly—Gly—Val—Val—Lys—
Asp—Asn—Phe—Val—Pro—Thr—Asn—Val—Gly—Ser—Lys—Ala—
Phe—Gly (Amara et al., Science, 229,1094 (1985))

(14) Hormone having angiotonic and hyperphagia effect (Neuro peptide, NPY)
Tyr-Pro-Ser-Lys-Pro-Asp-Asn-Pro-Gly-Glu-Asp-Met-Ala-Arg-Tyr-Tyr-Ser-Ala-Leu-Arg-His-Tyr-Ile-Asn-Leu-Ile-Tyr-Arg-Gln-Arg-Tyr
(Tatemoto et al., Proc. Natl. Acad. Sci. USA., 79,5485 (1982))

(15) Growth hormone-releasing factor (GRF)
Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Gln-Ser-Asn-Gln-Glu-Arg-Gly-Ala-Arg-Ala-Arg-Leu
(Mac Gillivray et al., Proc. Natl. Acad. Sci. USA, 79,2504 (1982))

(16) Secretion
His-Ser-Asp-Gly-Thr-Phe-Thr-Ser-Glu-Ser-Arg-Leu-Arg-Asp-Ser-Ala-Arg-Leu-Gln-Arg-Leu-Leu-Gln-Gly-Leu-Val
(Mutt et al., Biochem. Biophys. Res. Commin., 9,275 (1962))

(17) Hormone having hypotensive effect (VIP)
His-Ser-Asp-Ala-Val-Phe-Thr-Asp-Asn-Try-Thr-Arg-Leu-Arg-Lys-Gln-Met-Ala-Val-Lys-Lys-Tyr-Leu-Asn-Ser-Ile-Leu-Asn
(Said et al., Eur. J. Biochem., 28,199 (1972))

(18) Hormone PHI having angiectatic and insulin-secretomotory effect (peptide HI)
His-Ala-Asp-Gly-Val-Phe-Thr-Ser-Asp-Phe-Ser-Arg-Leu-Leu-Gly-Gln-Leu-Ser-Ala-Lys-Lys-Thr-Leu-Glu-Ser-Leu-Ile
(Tatemoto et al., Proc. Natl. Acad. Sci. USA, 75,4115 (1978))

(19) Gastrin-releasing peptide (GRP)
Val-Pro-Leu-Pro-Ala-Gly-Gly-Gly-Thr-Val-Leu-Thr-Lys-Met-Thr-Pro-Arg-Gly-Asn-His-Trp-Ala-Val-Gly-His-Leu-Met
(McDonald et al., Biochem. Biophys. Res. Commun., 90,227 (1979))

(20) Cholecystokinin (CCK)
Lys-Ala-Pro-Ser-Gly-Arg-Met-Ser-Ile-Val-Lys-Asn-Leu-Gln-Asn-Leu-Asp-Pro-Ser-His-Arg-Ile-Ser-Asp-Arg-Asp-Try(SO$_3^-$)-Met-Gly-Trp-Met-Asp-Phe-Gly-Arg-Arg-Ser-Ala-Glu
(Mutt et al., Biochem. J., 125,57, (1971))

(21) Hormone PYY suppressing pancreatic juice secretion
Tyr-Pro-Ala-Lys-Pro-Glu-Ala-Pro-Gly-Glu-Asp-Ala-Ser-Pro-Glu-Glu-Leu-Ser-Arg-Trgr-Ala-Ser-Leu-Arg-His-Tyr-Leu-Asn-Leu-Val-Thr-Arg-Gln-Arg-Tyr
(Tatemoto et al., Nature, 285,417 (1980))

(22) Gastric motor activity-stimulating hormone (motilin)
Phe-Val-Pro-Ile-Phe-Thr-Tyr-Gly-Glu-Leu-Gln-Arg-Met-Gln-Glu-Lys-Glu-Arg. Asn-Lys-Gly-Gln
(Brown; Can. J. Physiol. Pharmacol., 49,399, (1971))

Consequently, where genes which code for the above-mentioned physiologically active polypeptides are expressed in an adequate host cell, the fused polypeptides of the present invention are genetic products in which genes, for example, which code for proteins (if necessary, including adequate cleavable portions) which make them easily detected, and the above-mentioned genes are artificially ligated. These proteins include β-galactosidase, chloramphenicol acetyltransferase, and the like.

Utilizing the aqueous solution of crude polypeptides prepared as described above, the process of the present invention is preferably carried out while monitoring the objective polypeptides by using the RIA method or HPLC method. Where the fused polypeptides are obtained as precursors of the objective polypeptides, it is necessary to cleave the objective polypeptide moieties and other protein moieties fused thereto as described above, to prepare an aqueous solution containing the crude polypeptides of the present invention. Techniques for this cleavage may be selected according to the type of polypeptide, but generally processes of treating with CNBr, trypsin, collagenase, etc., are applicable. In this case, to inhibit non-specific peptidase activity, it is preferred to add an adequate amount of protease inhibitors, such as N-ethylmaleimide (NEM), dithiothreitol (DTT), 2-mercaptoethanol (2-ME), ethylenediamine tetraacetic acid (EDTA), or phenylmethanesulfonylfluoride (PMSF).

The reaction product, i.e., an aqueous solution containing crude polypeptides of the present invention, is then purified in a purification stage. For example, in a reaction solution of crude polypeptides obtained by cleaving with collagenase, formic acid, acetic acid, hydrochloric acid, or an aqueous solution thereof is added to adjust the pH to 1–4, preferably about pH 2. If the pH level exceeds 4, immanent protease, or non-specific protease, which possibly co-exists in the collagenase, adversely affects the stability of the objective physiologically active polypeptides, and the impurities to be removed may not be sufficiently modified and precipitated. If the pH level is less than 1, a precipitation of the objective polypeptides may occur, which would result in a worsened recovery rate. As the acid, formic acid is most preferable. The impurities thus precipitated are filtered or subjected to centrifugal separation. For example, after the solution is left to stand, the impurities precipitated by centrifugal separation are removed, thereby obtaining a supernatant having objective polypeptides dissolved therein. With regard to the revolution number of the centrifugal separation at this time, the stage is advantageously carried out at 1000 to 100000, preferably 5000 to 30000.

If the separation is carried out at the revolution number of less than 1000, an insufficient removal of the impurities may occur. Even if the revolution number is more than 100000, no significant effect can be obtained.

The above-mentioned stage is preferably carried out at a temperature equal to or less than normal room temperature, particularly at 1° to 15° C. If the temperature is less than 0° C., the solution is frozen, and the stability of the polypeptides worsened when being they are melted again. On the other hand, if the temperature exceeds 15° C., the stabilities of the objective polypeptides may be worsened. The period for treating with the acid is from several minutes to several hours, and usually a sufficient effect can be obtained at about 30 minutes. If the treatment period is less than several minutes, the impurities may be insufficiently removed. A treatment period over several hours gives no significant added effect.

The acid solution having the objective polypeptides dissolved therein obtained in the former stage is then adsorbed on a packing material for reversed phase high performance liquid chromatography. Any adsorption method able to bring a carrier into contact with the polypeptide in the solution can be applied as a means for adsorption. For example, an adsorption method in which an adequate amount of carrier is incorporated in a solution having a desired polypeptide dissolved therein, the contact being promoted by stirring or shaking to be adsorbed, an adsorption method in which a carrier is packed in a tube made of a suitable material, the polypeptide solution being passed through the tube to be adsorbed, an adsorption method in which a carrier is set as a filter bed, the peptide solution being passed and adsorbed thereon by pouring it thereon, etc., may be mentioned, but the method is not limited thereto as long as the peptide is brought into contact with a carrier, to thereby adsorb the peptide on the carrier.

As the packing material for reversed phase high performance liquid chromatography, a material in which cyanol groups having substituents of various carbon numbers being bonded on its surface can be used. Examples of commercially available products include CAPCELL PAK $C_{18}$ SG 300, CAPCELL PAK $C_8$ SG 300, CAPCELL PAK $C_{18}$ AG 120, and CAPCELL PAK $C_8$ AG 120 (all produced by Shiseido), Superpacks ferisoap ODS2 (produced by Pharmacia), TSK gel ODS-80TM, TSK gel ODS-120A, and TSK gel ODS-120T (all produced by Tosoh), Hipore RP-304 $C_4$ and Hipore RP-318 $C_{18}$ (both produced by Bio-Rad Laboratory), and the like.

The elution of the polypeptide adsorbed can be carried out after washing with an aqueous 0.1% trifluoroacetic acid solution (for amino acid analysis), by changing the polarity of the adsorbed polypeptide with a polar solvent such as acetonitrile, methanol, or butanol.

EXAMPLE

The present invention will now be described in detail with reference to the working examples, but the present invention is not to be limited thereto.

Example: Purification of Human Calcitonin Precursor Produced by Transforming E. coli Preparation of fused Polypeptide (Referential Example)

To obtain a human calcitonin precursor (which was then amidated at the C terminal to be human calcitonin), a gene which codes for human calcitonin-collagenase cleavage portion peptide-β-galactosidase fused polypeptide was prepared and the gene was incorporated in E. coli to be expressed. The transformed microorganism was cultivated in the manner described below.

To be specific, E. coli M15 strain transformed with plasmid pZT32 (Japanese Patent Application No. 63-226288) was cultivated in an amount of 20 l using a 30 l Jarfermenter (produced by Hitachi Seisakusho).

The following medium was used.

| | |
|---|---|
| $Na_2HPO_4.12H_2O$ | 1.8% |
| $KH_2PO_4$ | 0.2% |
| $(NH_4)_2SO_4$ | 0.2% |
| Yeast extract | 0.5% |
| Pepton (Difco) | 0.5% |
| $MgSO_4./7H_2O$ | 0.01% |
| Glucose | 0.5% |
| Ampicillin | 150 µg/ml |

500 ml of fungus liquid, which had been pre-cultivated on an LB-medium (T. Maniatis et al.; Molecular Cloning p48 (1982)) containing 150 µg/ml of ampicillin at 30° C. overnight, was transferred on 500 ml of the above-mentioned medium, and then cultivated at 30° C. The cultivation was continued while ventilating air at 1 vvm and adjusting the pH of the medium to 7.0 with sodium hydroxide. When it was cultivated for 3 hours, $OD_{660}$ became 1, whereby IPTG was added in a concentration of 1 mM. The cultivation was continued for 6 more hours, whereby $OD_{660}$ reached 10, and the fungi were collected by centrifugal separation. After being washed with sterilized water, the fungus bodies were suspended in 10 mM Tris-HCl bubber (pH 8.0)/1 mM EDTA/0.1 mM DTT, and were homogenized by using a homogenizer 15HR (produced by Goring) at 10° C. The supernatant obtained by centrifugal separation was taken as a cell extract solution.

Using β-galactosidase as an index, purification of human calcitonin-fused polypeptide was carried out.

Figure 4:
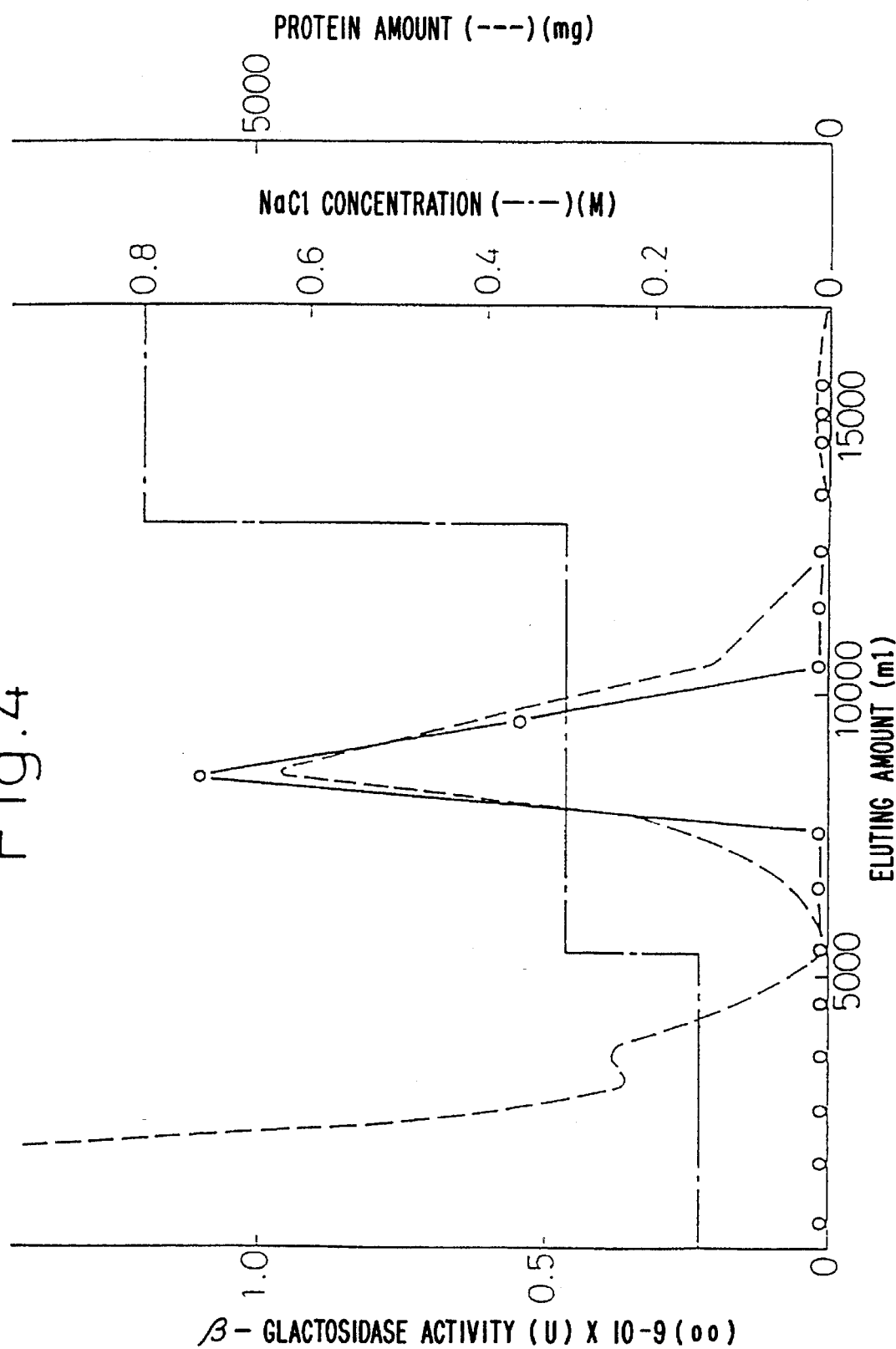
FIG. 4 shows an elution pattern of a human calcitonin fused polypeptide using an ion-exchange column chromatography.

First, low molecular proteins, etc., were removed by ultrafiltration (product name: Pelican cassette) using a Millipore type PT filter (fractionation molecular weight= 300000), and then the extract was further purified by ion-exchange chromatography using a DEAE-TOYOPLARL 650C (produced by Tosoh). As the eluent buffer, 10 mM Tris-HCl buffer (pH 7.4)/0.1 mM EDTA/0.1 mM DTT was used. When non-adsorbed proteins were eluted (1000 ml), adsorbed proteins were eluted by a gradual concentration gradient of sodium chloride. The concentrations of sodium chloride at this time were 0.16M, 0.32M, and 0.8M. The elution pattern is shown in FIG. 4. In the Figure, the concentration of sodium chloride is shown as _____. In FIG. 4, the β-galactosidase activity measured according to Miller's method (Miller. J., Experiments in molecular genetics 352–355 (1972)) is shown as o————o, and the amount of protein measured at an absorbency of 280 nm is shown as - - - - - -. The activity peaks were observed at a region of 1800–4500 ml of 0.32M Sodium chloride eluted fractionation. Consequently, this eluted fractionation was defined as the purified protein fractionation. The amount of protein was measured according to Lowry's method (Lowry, O. H. et al., J. Biol. Chem., 193, 265 (1951)). The calibration curve for Lowry's method was prepared by using a bovine-serum albumin (produced by Sigma, Fraction V).

Here, 1 unit of β-galactosidase was defined as a titer in which it works on o-nitrophenol β-D-galactoside at pH 7.0 at 28° C. to liberate 1 nmol of o-nitrophenyl for 1 minute.

Behaviors of specific activities by the above-mentioned treatment are shown in Table 1.

TABLE 1

| Step | Total Protein Amount (mg) | β-Galactosidase (U/mg) | Yeild (%) |
| --- | --- | --- | --- |
| Cell extract | 42200 | 63500 | 100 |
| Ultrafiltration | 22800 | 76900 | 65 |
| DEAE Toyoparl 650C | 9100 | 222000 | 39 |

The specific activity was increased about 3.5 times and was 222,000 U/mg protein.

Preparation of Crude Polypeptide by Specific decomposition of Fused Polypeptide

The above-mentioned human calcitonin-collagenase cleavage portion peptide-β-galactosidase fused polypeptide was specifically decomposed by using collagenase to obtain a C-terminal glycine adduct of human calcitonin. The collagenase used was available from Sigma (Type VII). The composition of the reaction solution is shown as follows:

5 mM Calcium chloride 50 mM Tris-HCl buffer, pH 7.5

250 μM Zinc chloride 10 mM Dithiothreitol 10 mM 2-Mercaptoethanol 1 mg/ml Fused protein purified standard 100 unit/ml Collagenase An enzyme reaction was carried out at 37° C. for 3 hours, and the reaction product was confirmed with HPLC. This reaction solution was designated as the "aqueous solution containing a crude polypeptide". The conditions of HPLC analysis were as follows:

By using CAPCELL PAK $C_{18}$ SG 300 (6 mm×35 mm) (produced by Shiseido) as a column, using an aqueous 0.1% trifluoroacetic acid solution/0.085% trifluoroacetic acid acetonitrile solution as an eluent, and linearly increasing the concentration of the 0.085% trifluoroacetic acid acetonitrile solution to 60% over a period of 20 minutes at a flow rate of 1.5 ml/min., a calcitonin precursor was eluted at an acetonitrile concentration of about 40%. The detection wavelength at this time was 214 nm.

Example 1: Purification of Crude Polypeptide

To the above-mentioned reaction solution containing the crude polypeptide, formic acid was added to a 2% concentration, and the solution was stirred, after which it was left to stand for 30 minutes at 4° C. After confirming that impurities had been sufficiently removed, the solution was centrifuged at 12000 rpm for 10 minutes to obtain a supernatant. The HPLC elution pattern of the supernatant at this time is shown in FIG. 1 (a). A filter paper (produced by Toyo Roshi, No. 2) was placed on a magnet Buchner funnel, and 10 g of CAPCELL PAK $C_8$SG 300 powder (produced by Shiseido) was placed thereon, and the funnel was placed on a suction bottle. The supernatant was gently poured into the above-mentioned Buchner funnel under suction. The HPLC elution pattern of the non-adsorbed fraction at this time is shown in FIG. 1 (b). After the suction was finished, the residue was washed with 50 ml of aqueous 0.1% trifluoroacetic acid solution (produced by Wako Junyaku, for amino acid analysis) in two portions (HPLC elution pattern of the eluate; FIG. 1 (c)). It was then washed with 50 ml of aqueous 0.1% trifluoroacetic acid/20% acetonitrile solution in two portions (HPLC elution pattern of the eluate; FIG. 1 (d)). Thereafter, the objective polypeptide was eluted with 5 ml of aqueous 0.1% trifluoroacetic acid/60% acetonitrile solution in ten portions (HPLC elution pattern of the eluate; FIG. 1 (e)); and finally the adsorbed substance was completely eluted with methanol (for HPLC analysis: produced by Nakaraitesk). The results of the purification are shown in Table 2. The purity is shown as a percentage by weight of human calcitonin precursor in the total protein. The purify after the treatment with formic acid was calculated from the sum of peaks I and II in FIG. 2. The purity was improved 56-fold by the formic acid treatment after the collagenase reaction, and 100% of human calcitonin precursor could be recovered. Also, the purity was further improved by more than 70% with the next treatment of CAPCELL PAK $C_8$ SG 300, attaining a 97% recovery.

TABLE 2

| Step | Human Calcitonin precursor (mg) | Purity (%) | Yield (%) |
| --- | --- | --- | --- |
| Collagenase cleavage | 120 | 0.9 | 100 |
| Treatment with formic acid | 120 | 51 | 100 |
| Treatment with CAPCELL PAK $C_8$ SG 300 | 115 | >70 | 97 |

FIG. 2 is a drawing which shows an elution pattern when the eluate of FIG. 1 (e), after being freeze-dried, is analyzed with HPLC. As is clear from this figure, there are four strong peaks for objective polypeptide in the elution pattern of HPLC analysis. They are due to the change of the N-terminal portion during the collagenase reaction. Each peak was analyzed by a peptide sequencer (produced by ABI, Model 471). According to the analysis, it was found that peaks I and II corresponded to human calcitonin precursors having 1 to 33 amino acids, peak III corresponded to that in which 1–7 positions in the N-terminal were deleted, and peak IV corresponded to that in which 1–8 positions in the N-terminal were deleted. In addition, peak II was found to correspond to that in which the S—S bonds in 1- and 7-positions had been reduced.

Figure 3:
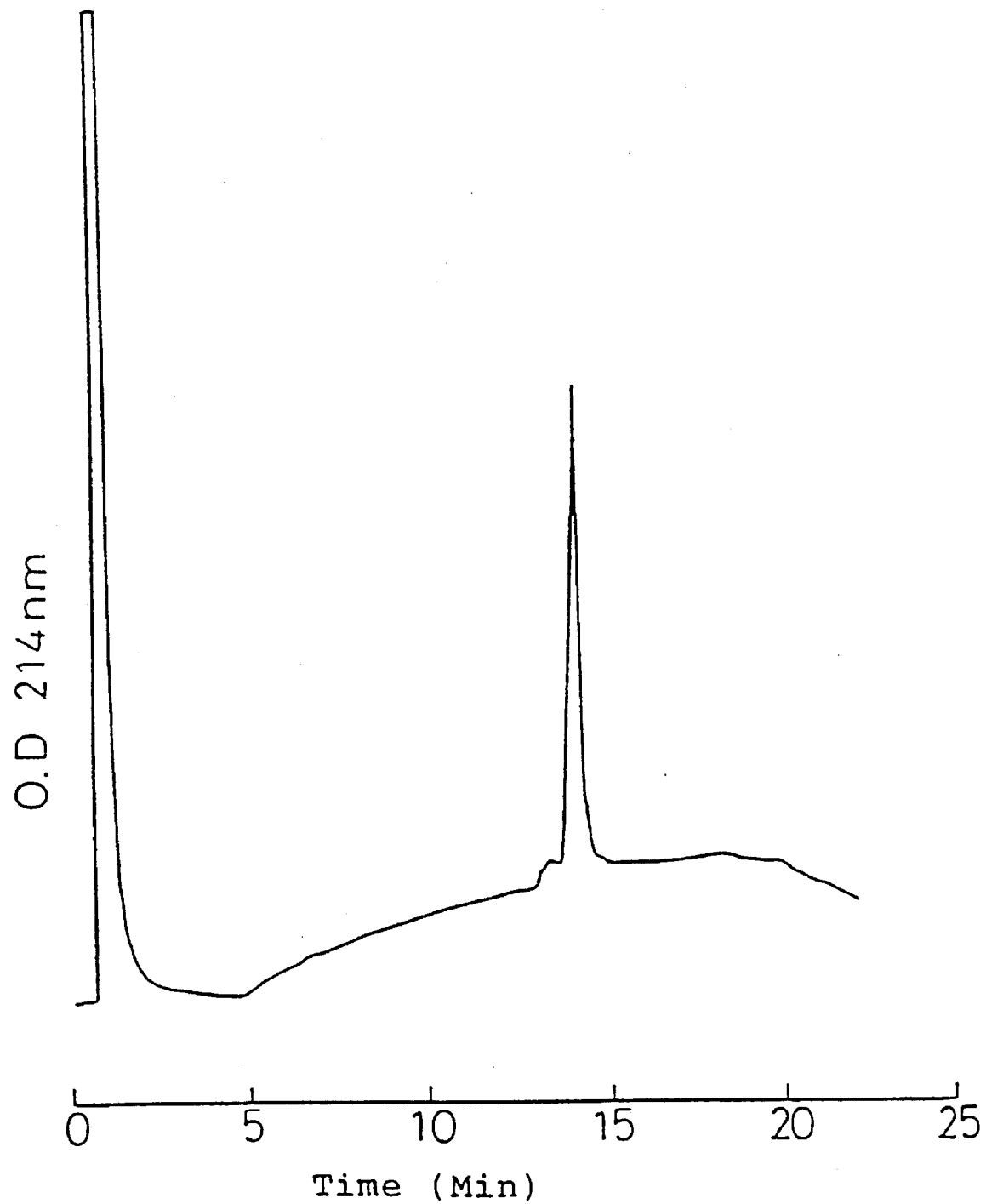
FIG. 3 shows an HPLC elution pattern of the highly pure purified human calcitonin precursor obtained by dispensing the solution of FIG. 2.

Analytical results, after which both the purification process of the present invention and an HPLC dispensing procedure were carried out, are shown in FIG. 3.

On the other hand, using the above-mentioned reaction solution containing the crude polypeptide, a purification of polypeptide was carried out by a conventional ion-exchanging column and HPLC as a comparative example. In this case, ten stages were required for the purification. Each stage required 2 hours, and therefore, a total of 10 times the required period of Example 1 according to the present invention was required.

Examples 2 and 3

Figure 5:
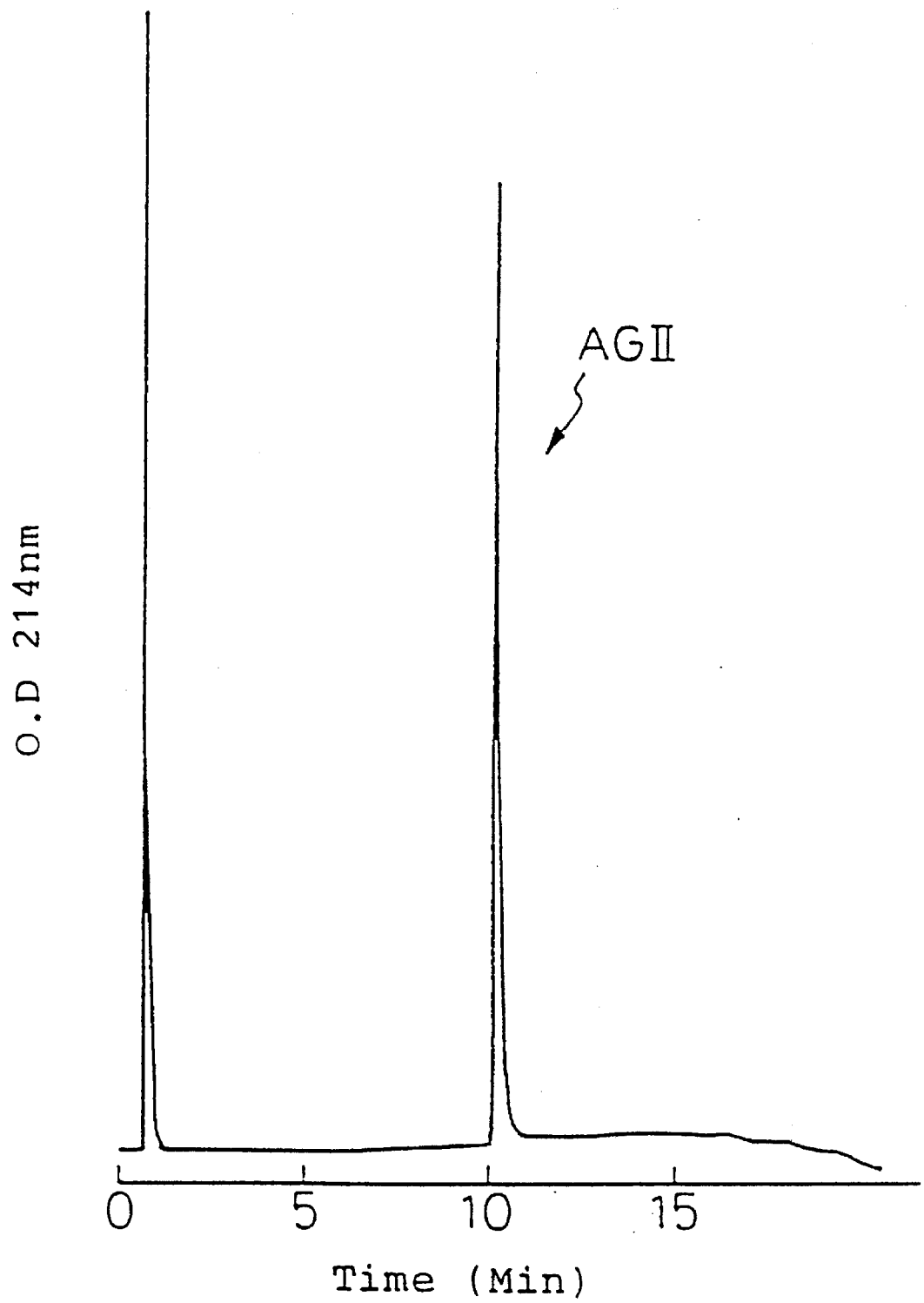
FIG. 5 shows an HPLC elution pattern of an eluate purified according to the process of the present invention.
Figure 6:
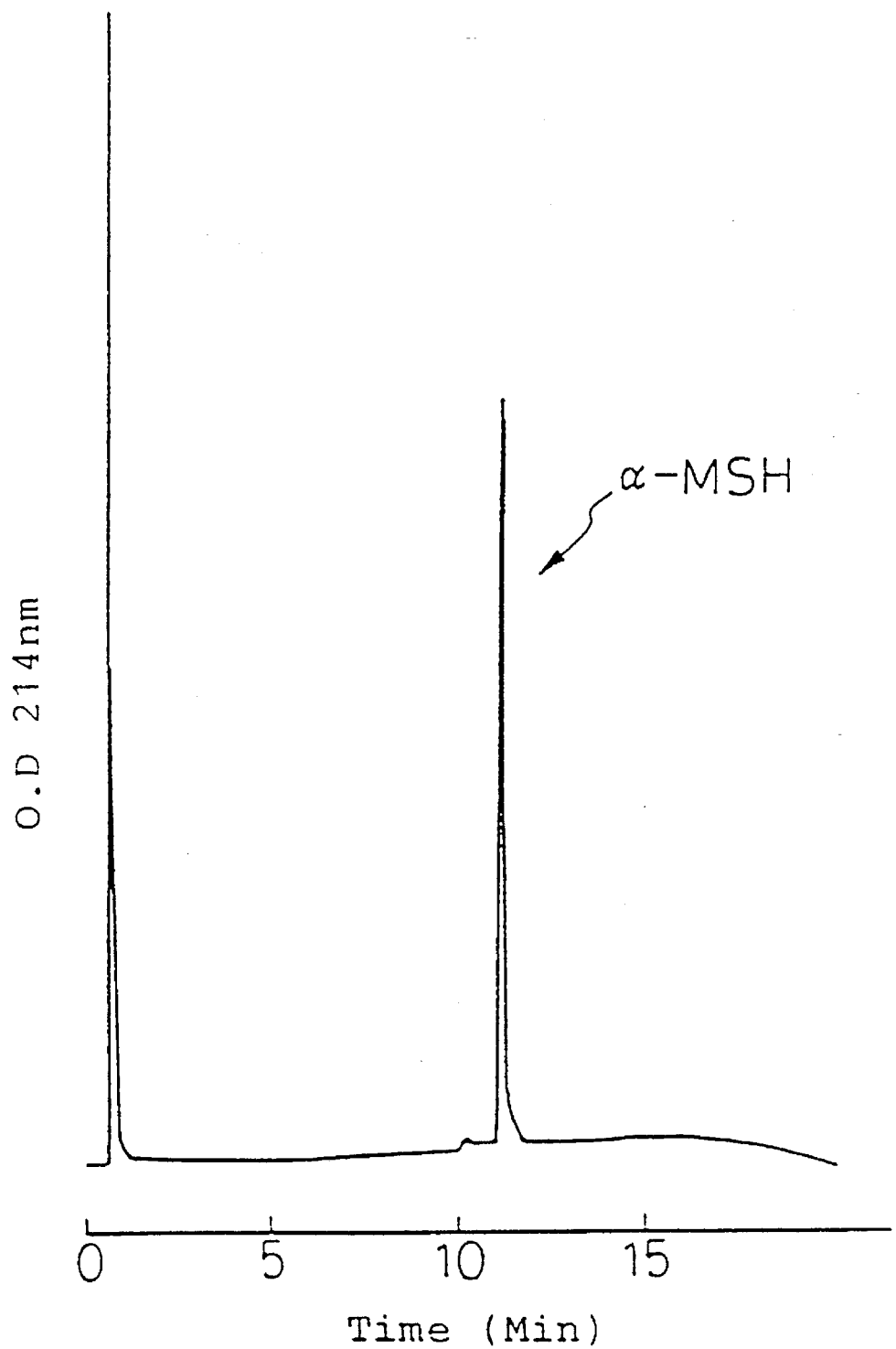
FIG. 6 shows an HPLC elution pattern of melanocyte-stimulating hormone eluate purified according to the process of the present invention.

According to the expression of the gene coding for human calcitonin-collagenase cleavage portion peptide-β-galactosidase fused polypeptide by E. coli, and the purification procedure of Example 1, angiotensin II-collagenase cleavage portion peptide-β-galactosidase fused polypeptide, and melanocyte-stimulating hormone-collagenase cleavage portion peptide-β-galactosidase fused polypeptide were produced and an aqueous solution containing a polypeptide was prepared in each case. These solutions were treated in the same manner as that of Example 1. The HPLC elution patterns of eluates for angiotensin II and melanocyte-stimulating hormone are shown in FIG. 5 and FIG. 6, respectively.

[INDUSTRIAL APPLICABILITY]

The process of the present invention can be advantageously carried out in any purification stage in the production of various polypeptides, especially physiologically active polypeptides.

We claim:

1. A process for purifying a polypeptide, which comprises the steps of:

(a) regulating the pH range of an aqueous solution containing a crude polypeptide to 1–4 using formic acid, to cause impurities to precipitate, followed by removing these impurities leaving a supernatant, wherein said crude polypeptide is a reaction solution in which a fused polypeptide is cleaved into physiologically active moieties having a molecular weight of not more than 15,000 and another protein moiety fused thereto, wherein said physiologically active moiety is selected from the group consisting of insulin, growth hormone release factor, epidermal growth factor, atrial natriuretic peptide, thymosin $\alpha_1$, thymosin $\beta_4$, thymopoietin, transforming growth factor, adrenocorticotropic hormone, calcitonin gene-related peptide, and cartilage factor;

and said other protein moiety is selected from the group consisting of β-galactosidase and chloramphenicol acetyltransferase; which is directly followed by (b) adsorbing the supernatant on a packing material for reversed phase high performance liquid chromatography by pouring said supernatant into a Buchner funnel into which said packing material has been placed, followed by eluting the desired polypeptides.

* * * * *

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( i i i ) HYPOTHETICAL: YES ( x i ) SEQUENCE DESCRIPTION: SEQ ID NO:1:

Asp  Arg  Val  Tyr  Ile  His  Pro  Phe
1                   5

( 2 ) INFORMATION FOR SEQ ID NO:2:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( i i i ) HYPOTHETICAL: YES ( x i ) SEQUENCE DESCRIPTION: SEQ ID NO:2:

Ser  Arg  Val  Tyr  Val  His  Pro  Ala
1                   5

( 2 ) INFORMATION FOR SEQ ID NO:3:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( i i i ) HYPOTHETICAL: YES ( x i ) SEQUENCE DESCRIPTION: SEQ ID NO:3:

Arg  Val  Tyr  Ile  His  Pro  Phe
1              5

( 2 ) INFORMATION FOR SEQ ID NO:4:

( i ) SEQUENCE CHARACTERISTICS:
( A ) LENGTH: 33 amino acids
( B ) TYPE: amino acid
( D ) TOPOLOGY: linear ( i i ) MOLECULE TYPE: peptide ( i i i ) HYPOTHETICAL: YES (vi) ORIGINAL SOURCE:
    (A) ORGANISM: Human (xi) SEQUENCE DESCRIPTION: SEQ ID NO:4:

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

Gly (2) INFORMATION FOR SEQ ID NO:5:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (iii) HYPOTHETICAL: YES (vi) ORIGINAL SOURCE:
        (A) ORGANISM: Swine (xi) SEQUENCE DESCRIPTION: SEQ ID NO:5:

Cys Ser Asn Leu Ser Thr Cys Val Leu Ser Ala Tyr Trp Arg Asn Leu
1               5                   10                  15

Asn Asn Phe His Arg Phe Ser Gly Met Gly Phe Gly Pro Glu Thr Pro
            20                  25                  30

Gly (2) INFORMATION FOR SEQ ID NO:6:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (iii) HYPOTHETICAL: YES (vi) ORIGINAL SOURCE:
        (A) ORGANISM: Bovine (xi) SEQUENCE DESCRIPTION: SEQ ID NO:6:

Cys Ser Asn Leu Ser Thr Cys Val Leu Ser Ala Tyr Trp Lys Asp Leu
1               5                   10                  15

Asn Asn Thr His Arg Phe Ser Gly Met Gly Phe Gly Pro Glu Thr Pro
            20                  25                  30

Gly (2) INFORMATION FOR SEQ ID NO:7:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (iii) HYPOTHETICAL: YES (vi) ORIGINAL SOURCE:
        (A) ORGANISM: Salmon (xi) SEQUENCE DESCRIPTION: SEQ ID NO:7:

```
        Cys  Ser  Asn  Leu  Ser  Thr  Cys  Val  Leu  Gly  Lys  Leu  Ser  Gln  Glu  Leu
        1                   5                        10                       15

His  Lys  Leu  Gln  Thr  Tyr  Pro  Arg  Thr  Asn  Thr  Gly  Ser  Gly  Thr  Pro
                        20                       25                       30

Gly
```

(2) INFORMATION FOR SEQ ID NO:8:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (iii) HYPOTHETICAL: YES (vi) ORIGINAL SOURCE:
        (A) ORGANISM: Rabbit (xi) SEQUENCE DESCRIPTION: SEQ ID NO:8:

```
        Cys  Ser  Asn  Leu  Ser  Thr  Cys  Val  Leu  Gly  Lys  Leu  Ser  Gln  Glu  Leu
        1                   5                        10                       15

His  Lys  Leu  Gln  Thr  Tyr  Pro  Arg  Thr  Asp  Val  Gly  Ala  Gly  Thr  Pro
                        20                       25                       30

Gly
```

(2) INFORMATION FOR SEQ ID NO:9:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (iii) HYPOTHETICAL: YES (vi) ORIGINAL SOURCE:
        (A) ORGANISM: Avian (xi) SEQUENCE DESCRIPTION: SEQ ID NO:9:

```
        Cys  Ala  Ser  Leu  Ser  Thr  Cys  Val  Leu  Gly  Lys  Leu  Ser  Gln  Glu  Leu
        1                   5                        10                       15

His  Lys  Leu  Gln  Thr  Tyr  Pro  Arg  Thr  Asp  Val  Gly  Ala  Gly  Thr  Pro
                        20                       25                       30

Gly
```

(2) INFORMATION FOR SEQ ID NO:10:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (iii) HYPOTHETICAL: YES (xi) SEQUENCE DESCRIPTION: SEQ ID NO:10:

```
        Ser  Tyr  Ser  Met  Glu  His  Phe  Arg  Trp  Gly  Lys  Pro  Val
        1                   5                        10
```

(2) INFORMATION FOR SEQ ID NO:11:

(i) SEQUENCE CHARACTERISTICS:
        (A) LENGTH: 16 amino acids (B) TYPE: amino acid
(D) TOPOLOGY: linear (ii) MOLECULE TYPE: peptide (iii) HYPOTHETICAL: YES (xi) SEQUENCE DESCRIPTION: SEQ ID NO:11:

| Asp | Gly | Asp | Asp | Tyr | Lys | Phe | Gly | His | Phe | Arg | Trp | Ser | Val | Pro | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

(2) INFORMATION FOR SEQ ID NO:12:

(i) SEQUENCE CHARACTERISTICS:
(A) LENGTH: 56 amino acids
(B) TYPE: amino acid
(D) TOPOLOGY: linear (ii) MOLECULE TYPE: peptide (iii) HYPOTHETICAL: YES (vi) ORIGINAL SOURCE:
(A) ORGANISM: Human (xi) SEQUENCE DESCRIPTION: SEQ ID NO:12:

| Asp | Ser | Leu | Gly | Arg | Glu | Ala | Lys | Cys | Tyr | Asn | Glu | Leu | Asn | Gly | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Lys | Ile | Tyr | Asn | Pro | Val | Cys | Gly | Thr | Asp | Gly | Asp | Thr | Tyr | Pro |
|     |     |     | 20  |     |     |     |     | 25  |     |     |     |     | 30  |     |     |

| Asn | Gly | Cys | Val | Leu | Cys | Phe | Gly | Asn | Arg | Lys | Arg | Gln | Thr | Ser | Ile |
|     |     | 35  |     |     |     |     | 40  |     |     |     |     | 45  |     |     |     |

| Leu | Ile | Gln | Lys | Ser | Gly | Pro | Cys |
|     | 50  |     |     |     |     | 55  |     |

(2) INFORMATION FOR SEQ ID NO:13:

(i) SEQUENCE CHARACTERISTICS:
(A) LENGTH: 56 amino acids
(B) TYPE: amino acid
(D) TOPOLOGY: linear (ii) MOLECULE TYPE: peptide (iii) HYPOTHETICAL: YES (vi) ORIGINAL SOURCE:
(A) ORGANISM: Bovine (xi) SEQUENCE DESCRIPTION: SEQ ID NO:13:

| Asn | Ile | Leu | Gly | Arg | Glu | Ala | Lys | Cys | Thr | Asn | Glu | Val | Asn | Gly | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Pro | Arg | Ile | Tyr | Asn | Pro | Val | Cys | Gly | Thr | Asp | Gly | Val | Thr | Tyr | Ser |
|     |     |     | 20  |     |     |     |     | 25  |     |     |     |     | 30  |     |     |

| Asn | Glu | Cys | Leu | Leu | Cys | Met | Glu | Asn | Lys | Glu | Arg | Gln | Thr | Pro | Val |
|     |     | 35  |     |     |     |     | 40  |     |     |     |     | 45  |     |     |     |

| Leu | Ile | Gln | Lys | Ser | Gly | Pro | Cys |
|     | 50  |     |     |     |     | 55  |     |

(2) INFORMATION FOR SEQ ID NO:14:

(i) SEQUENCE CHARACTERISTICS:
(A) LENGTH: 84 amino acids
(B) TYPE: amino acid
(D) TOPOLOGY: linear (ii) MOLECULE TYPE: peptide (i i i) HYPOTHETICAL: YES (v i) ORIGINAL SOURCE:
  (A) ORGANISM: Swine (x i) SEQUENCE DESCRIPTION: SEQ ID NO:14:

```
Ser Val Ser Glu Ile Gln Leu Met His Asn Leu Gly Lys His Leu Ser
1               5                   10                  15

Ser Leu Glu Arg Val Gln Trp Leu Arg Lys Lys Leu Gln Asp Val His
            20                  25                  30

Asn Phe Val Ala Leu Gly Ala Ser Ile Val His Arg Asp Gly Gly Ser
        35                  40                  45

Gln Arg Pro Arg Lys Lys Glu Asp Asn Val Leu Val Glu Ser His Gln
        50              55                  60

Lys Ser Leu Gly Glu Ala Asp Lys Ala Ala Val Asp Val Leu Ile Lys
65                  70                  75                  80

Ala Lys Pro Gln
```

(2) INFORMATION FOR SEQ ID NO:15:

(i) SEQUENCE CHARACTERISTICS:
    (A) LENGTH: 8 amino acids
    (B) TYPE: amino acid
    (D) TOPOLOGY: linear (i i) MOLECULE TYPE: peptide (i i i) HYPOTHETICAL: YES (v i) ORIGINAL SOURCE:
    (A) ORGANISM: Swine (x i) SEQUENCE DESCRIPTION: SEQ ID NO:15:

```
Cys Tyr Phe Gln Asn Cys Pro Lys
1               5
```

(2) INFORMATION FOR SEQ ID NO:16:

(i) SEQUENCE CHARACTERISTICS:
    (A) LENGTH: 26 amino acids
    (B) TYPE: amino acid
    (D) TOPOLOGY: linear (i i) MOLECULE TYPE: peptide (i i i) HYPOTHETICAL: YES (v i) ORIGINAL SOURCE:
    (A) ORGANISM: Bovine (x i) SEQUENCE DESCRIPTION: SEQ ID NO:16:

```
Glu Val Glu Gly Pro Gln Val Gly Ala Leu Glu Leu Ala Gly Gly Pro
1               5                   10                  15

Gly Ala Gly Gly Leu Glu Gly Pro Pro Gln
            20                  25
```

(2) INFORMATION FOR SEQ ID NO:17:

(i) SEQUENCE CHARACTERISTICS:
    (A) LENGTH: 70 amino acids
    (B) TYPE: amino acid
    (D) TOPOLOGY: linear (i i) MOLECULE TYPE: peptide (i i i) HYPOTHETICAL: YES (x i) SEQUENCE DESCRIPTION: SEQ ID NO:17:

```
Gly Pro Glu Thr Leu Cys Gly Ala Glu Leu Val Asp Ala Leu Gln Phe
 1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
            35              40                  45

Phe Arg Ser Cys Asp Leu Arg Arg Leu Glu Met Tyr Cys Ala Pro Leu
        50              55                  60

Lys Pro Ala Lys Ser Ala
 65                  70
```

(2) INFORMATION FOR SEQ ID NO:18:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide ( i i i ) HYPOTHETICAL: YES ( v i ) ORIGINAL SOURCE:
        ( A ) ORGANISM: Avian ( x i ) SEQUENCE DESCRIPTION: SEQ ID NO:18:

```
Gly Pro Ser Gln Pro Thr Tyr Pro Gly Asp Asp Ala Pro Val Glu Asp
 1               5                   10                  15

Leu Ile Arg Phe Tyr Asp Asn Leu Gln Gln Tyr Leu Asn Val Val Thr
            20                  25                  30

Arg His Arg Tyr
         35
```

(2) INFORMATION FOR SEQ ID NO:19:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( i i i ) HYPOTHETICAL: YES ( v i ) ORIGINAL SOURCE:
        ( A ) ORGANISM: Human ( x i ) SEQUENCE DESCRIPTION: SEQ ID NO:19:

```
Ala Cys Asp Thr Ala Thr Cys Val Thr His Arg Leu Ala Gly Leu Leu
 1               5                   10                  15

Ser Arg Ser Gly Gly Val Val Lys Asn Asn Phe Val Pro Thr Asn Val
            20                  25                  30

Gly Ser Lys Ala Phe Gly
         35
```

(2) INFORMATION FOR SEQ ID NO:20:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( i i i ) HYPOTHETICAL: YES (v i) ORIGINAL SOURCE:
    (A) ORGANISM: Human (x i) SEQUENCE DESCRIPTION: SEQ ID NO:20:

| Ala | Cys | Asn | Thr | Ala | Thr | Cys | Val | Thr | His | Arg | Leu | Ala | Gly | Leu | Leu |
|---|---|---|---|---|---|---|---|---|---|---|---|---|---|---|---|
| 1 | | | | 5 | | | | | 10 | | | | | 15 | |

| Ser | Arg | Ser | Gly | Gly | Met | Val | Lys | Ser | Asn | Phe | Val | Pro | Thr | Asn | Val |
|---|---|---|---|---|---|---|---|---|---|---|---|---|---|---|---|
| | | | 20 | | | | | 25 | | | | | 30 | | |

| Gly | Ser | Lys | Ala | Phe | Gly |
|---|---|---|---|---|---|
| | | 35 | | | |

(2) INFORMATION FOR SEQ ID NO:21:

(i) SEQUENCE CHARACTERISTICS:
      (A) LENGTH: 38 amino acids
      (B) TYPE: amino acid
      (D) TOPOLOGY: linear (i i) MOLECULE TYPE: peptide (i i i) HYPOTHETICAL: YES (v i) ORIGINAL SOURCE:
      (A) ORGANISM: Rat (x i) SEQUENCE DESCRIPTION: SEQ ID NO:21:

| Ser | Cys | Asn | Thr | Ala | Thr | Cys | Val | Thr | His | Arg | Leu | Ala | Gly | Leu | Leu |
|---|---|---|---|---|---|---|---|---|---|---|---|---|---|---|---|
| 1 | | | | 5 | | | | | 10 | | | | | 15 | |

| Ser | Arg | Ser | Gly | Gly | Val | Val | Lys | Asp | Asn | Phe | Val | Pro | Thr | Asn | Val |
|---|---|---|---|---|---|---|---|---|---|---|---|---|---|---|---|
| | | | 20 | | | | | 25 | | | | | 30 | | |

| Gly | Ser | Glu | Ala | Phe | Gly |
|---|---|---|---|---|---|
| | | 35 | | | |

(2) INFORMATION FOR SEQ ID NO:22:

(i) SEQUENCE CHARACTERISTICS:
      (A) LENGTH: 38 amino acids
      (B) TYPE: amino acid
      (D) TOPOLOGY: linear (i i) MOLECULE TYPE: peptide (i i i) HYPOTHETICAL: YES (v i) ORIGINAL SOURCE:
      (A) ORGANISM: Rat (x i) SEQUENCE DESCRIPTION: SEQ ID NO:22:

| Ser | Cys | Asn | Thr | Ala | Thr | Cys | Val | Thr | His | Arg | Leu | Ala | Gly | Leu | Leu |
|---|---|---|---|---|---|---|---|---|---|---|---|---|---|---|---|
| 1 | | | | 5 | | | | | 10 | | | | | 15 | |

| Ser | Arg | Ser | Gly | Gly | Val | Val | Lys | Asp | Asn | Phe | Val | Pro | Thr | Asn | Val |
|---|---|---|---|---|---|---|---|---|---|---|---|---|---|---|---|
| | | | 20 | | | | | 25 | | | | | 30 | | |

| Gly | Ser | Lys | Ala | Phe | Gly |
|---|---|---|---|---|---|
| | | 35 | | | |

(2) INFORMATION FOR SEQ ID NO:23:

(i) SEQUENCE CHARACTERISTICS:
      (A) LENGTH: 31 amino acids
      (B) TYPE: amino acid
      (D) TOPOLOGY: linear (i i) MOLECULE TYPE: peptide (i i i) HYPOTHETICAL: YES (x i) SEQUENCE DESCRIPTION: SEQ ID NO:23:

```
        Tyr  Pro  Ser  Lys  Pro  Asp  Asn  Pro  Gly  Glu  Asp  Met  Ala  Arg  Tyr  Tyr
        1              5                        10                           15

Ser  Ala  Leu  Arg  His  Tyr  Ile  Asn  Leu  Ile  Tyr  Arg  Gln  Arg  Tyr
                       20                       25                      30
```

( 2 ) INFORMATION FOR SEQ ID NO:24:

( i ) SEQUENCE CHARACTERISTICS:
        ( A ) LENGTH: 44 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:24:

```
        Tyr  Ala  Asp  Ala  Ile  Phe  Thr  Asn  Ser  Tyr  Arg  Lys  Val  Leu  Gly  Gln
        1              5                        10                           15

Leu  Ser  Ala  Arg  Lys  Leu  Leu  Gln  Asp  Ile  Met  Ser  Arg  Gln  Gln  Gly
                       20                       25                      30

Gln  Ser  Asn  Gln  Glu  Arg  Gly  Ala  Arg  Ala  Arg  Leu
                       35                       40
```

( 2 ) INFORMATION FOR SEQ ID NO:25:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:25:

```
        His  Ser  Asp  Gly  Thr  Phe  Thr  Ser  Glu  Ser  Arg  Leu  Arg  Asp  Ser  Ala
        1              5                        10                           15

Arg  Leu  Gln  Arg  Leu  Leu  Gln  Gly  Leu  Val
                       20                       25
```

( 2 ) INFORMATION FOR SEQ ID NO:26:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:26:

```
        His  Ser  Asp  Ala  Val  Phe  Thr  Asp  Asn  Tyr  Thr  Arg  Leu  Arg  Lys  Gln
        1              5                        10                           15

Met  Ala  Val  Lys  Lys  Tyr  Leu  Asn  Ser  Ile  Leu  Asn
                       20                       25
```

( 2 ) INFORMATION FOR SEQ ID NO:27:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:27:

His Ala Asp Gly Val Phe Thr Ser Asp Phe Ser Arg Leu Leu Gly Gln
1               5                   10                  15

Leu Ser Ala Lys Lys Thr Leu Glu Ser Leu Ile
            20                  25

( 2 ) INFORMATION FOR SEQ ID NO:28:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:28:

Val Pro Leu Pro Ala Gly Gly Gly Thr Val Leu Thr Lys Met Thr Pro
1               5                   10                  15

Arg Gly Asn His Trp Ala Val Gly His Leu Met
            20                  25

( 2 ) INFORMATION FOR SEQ ID NO:29:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:29:

Lys Ala Pro Ser Gly Arg Met Ser Ile Val Lys Asn Leu Gln Asn Leu
1               5                   10                  15

Asp Pro Ser His Arg Ile Ser Asp Arg Asp Tyr Met Gly Trp Met Asp
            20                  25                  30

Phe Gly Arg Arg Ser Ala Glu
        35

( 2 ) INFORMATION FOR SEQ ID NO:30:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:30:

Tyr Pro Ala Lys Pro Glu Ala Pro Gly Glu Asp Ala Ser Pro Glu Glu
1               5                   10                  15

Leu Ser Arg Xaa Ala Ser Leu Arg His Tyr Leu Asn Leu Val Thr Arg
            20                  25                  30

Gln Arg Tyr
        35

( 2 ) INFORMATION FOR SEQ ID NO:31:

( i ) SEQUENCE CHARACTERISTICS:
        ( A ) LENGTH: 22 amino acids (B) TYPE: amino acid
(D) TOPOLOGY: linear (i i) MOLECULE TYPE: peptide (i i i) HYPOTHETICAL: YES (x i) SEQUENCE DESCRIPTION: SEQ ID NO:31:

Phe Val Pro Ile Phe Thr Tyr Gly Glu Leu Gln Arg Met Gln Glu Lys
1               5                   10                  15

Glu Arg Asn Lys Gly Gln
            20